United States Patent
Dittmer et al.

(10) Patent No.: US 10,413,639 B2
(45) Date of Patent: Sep. 17, 2019

(54) INTERNAL CERMET ROUTING FOR COMPLEX FEEDTHROUGHS

(71) Applicant: Heraeus Deutschland GmbH & Co. KG, Hanau (DE)

(72) Inventors: Robert Dittmer, Hanau (DE); Ulrich Hausch, Frankfurt am Main (DE); Jens Trötzschel, Ronneburg (DE); Peter Herzog, Biebergemünd (DE); Josef Roth, Bessenbach (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 16/151,821

(22) Filed: Oct. 4, 2018

(65) Prior Publication Data

US 2019/0105431 A1    Apr. 11, 2019

(30) Foreign Application Priority Data

Oct. 5, 2017   (EP) .................................... 17195022

(51) Int. Cl.
*A61L 31/12* (2006.01)
*A61N 1/375* (2006.01)
(Continued)

(52) U.S. Cl.
CPC .......... *A61L 31/124* (2013.01); *A61N 1/3754* (2013.01); *C04B 41/009* (2013.01);
(Continued)

(58) Field of Classification Search
CPC ... A61L 31/124; C04B 41/80; C04B 41/4578; C04B 2237/62; A61N 1/3754
(Continued)

(56) References Cited

U.S. PATENT DOCUMENTS

| 7,164,572 | B1 | 1/2007 | Burdon et al. |
| 8,894,914 | B2 | 11/2014 | Pavlovic |

(Continued)

FOREIGN PATENT DOCUMENTS

| DE | 102009035972 | 4/2011 |
| DE | 102011009861 | 8/2012 |

(Continued)

*Primary Examiner* — Sherman Ng
(74) *Attorney, Agent, or Firm* — Dicke, Billig & Czaja, PLLC

(57) ABSTRACT

One aspect relates to a composite, including a ceramic body having a first layer surface and a second layer surface and at least one cermet conductor that electrically connects the surfaces. The composite includes a first layer with the first layer surface, a first ceramic, a first hole and a first cermet element in the first hole, a second layer with the second layer surface, a second ceramic, a second hole and a second cermet element in the second hole, and an intermediate layer that is located between the first and the second layer. The intermediate layer includes an intermediate layer ceramic, an intermediate hole and one intermediate cermet element in the intermediate hole. A projection of the cross-section of the first hole and a projection of the cross section of the second hole onto a plane $P_{x,y}$ are arranged offset to each other.

16 Claims, 11 Drawing Sheets

(51) Int. Cl.
 *C04B 41/00* (2006.01)
 *C04B 41/45* (2006.01)
 *C04B 41/80* (2006.01)
(52) U.S. Cl.
 CPC ...... *C04B 41/0072* (2013.01); *C04B 41/4578* (2013.01); *C04B 41/80* (2013.01); C04B 2237/62 (2013.01)
(58) Field of Classification Search
 USPC ........................................................ 174/250
 See application file for complete search history.

(56) References Cited

U.S. PATENT DOCUMENTS

| | | | |
|---|---|---|---|
| 2005/0045268 A1 | 3/2005 | Yoshida et al. | |
| 2005/0079450 A1* | 4/2005 | Yoshida | G03F 7/20 430/322 |
| 2007/0060969 A1* | 3/2007 | Burdon | A61N 1/375 607/37 |
| 2007/0060970 A1* | 3/2007 | Burdon | A61N 1/3754 607/37 |
| 2012/0197326 A1* | 8/2012 | Pavlovic | H01R 43/20 607/5 |
| 2013/0032378 A1 | 2/2013 | Morioka et al. | |
| 2016/0287882 A1* | 10/2016 | Karst | H01L 23/057 |

FOREIGN PATENT DOCUMENTS

| | | |
|---|---|---|
| EP | 1897588 | 3/2008 |
| EP | 3041046 | 7/2016 |

* cited by examiner $$x_1 = x_2$$
$$y_1 \neq y_2$$

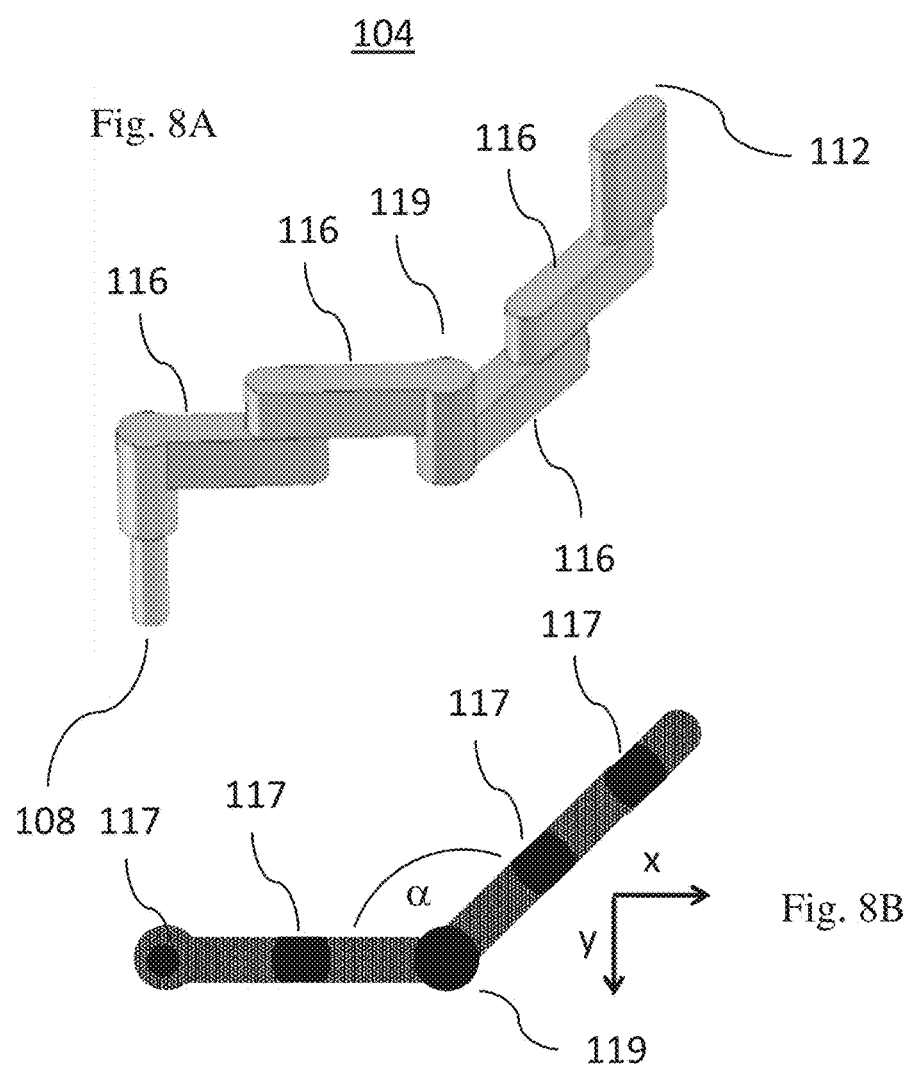

Fig. 9A
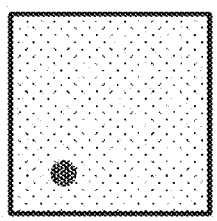 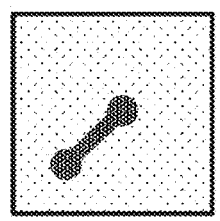 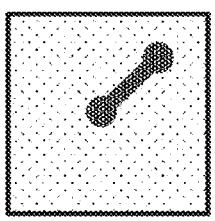 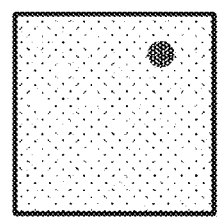
1  2  3  4
Fig. 9B
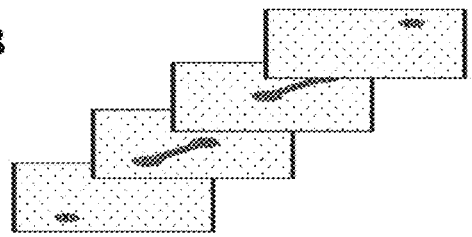
Fig. 9C

Fig. 10A
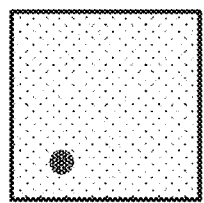 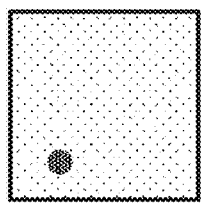 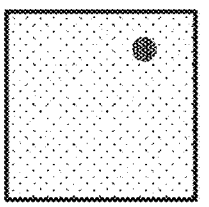 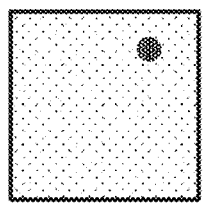
Fig. 10B 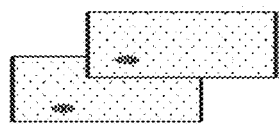 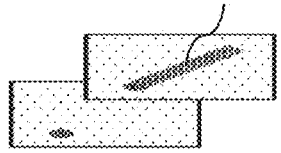 Fig. 10C

INTERNAL CERMET ROUTING FOR COMPLEX FEEDTHROUGHS

CROSS-REFERENCE TO RELATED APPLICATION

This Utility Patent Application claims priority to Application No. EP 17195022.3, filed on Oct. 5, 2017, which is incorporated herein by reference.

BACKGROUND

One embodiment relates to a composite including a ceramic multilayer body, including a cermet feedthrough; to a process for manufacturing a composite, including a cermet feedthrough; to a composite obtainable by the process; to a device including a composite according to one embodiment; and to a use of a composite.

The prior art knows numerous implantable electrical medical devices, for example pacemakers and defibrillators. Pacemakers known in the prior art include a bladder pacemaker, a breath pacemaker, an intestinal pacemaker, a diaphragm pacemaker, a cerebral pacemaker and a cardiac pacemaker. Such devices commonly include a housing enclosing electronics. An electrical source of energy, for example, a battery, may be included by the housing as well or it may be included by a further housing and be connected to the electronics via electrical connectors. The housing which is to be implanted into a human or animal body must hermetically seal the electronics from the surrounding body, that is, it must be leak tight for body fluids and gases. Commonly an object of an implantable electrical medical device involves electrically stimulating tissue, that is, muscles or brain cells, via electrodes or measuring electrical signals of the body via antennae, or both. Therefore, the implantable electrical medical device has to include an electrical feedthrough which electrically connects the inside of the housing to the outside. Such a feedthrough has to be designed to maintain the housing hermetically tight and thus the device implantable. Therefore, an electrical feedthrough for implantable medical devices commonly known in the prior art includes an electrically conductive feedthrough element, here a metal feedthrough wire, which is enclosed by a ceramic ring. Therein, the feedthrough wire is soldered to the ceramic ring via a gold solder. The ceramic ring in turn is soldered into a metal flange, which can be welded to a metal housing. The feedthrough assembly of the prior art includes several intermaterial connections which may be prone to breaking or leaking. In addition, establishing such intermaterial connections is costly or makes a production process more complicated or lengthy. An improved feedthrough is disclosed in EP 1 897 588 B1. Therein, the metal feedthrough wire is connected to a surrounding ceramic body by means of sintering. This way the number of intermaterial connections and the amount of gold solder used are reduced. The connection between the electrically conductive feedthrough element and the ceramic body could be improved by means of the disclosure of DE 10 2009 035 972 A1. Therein, a feedthrough element made of a cermet is used instead of a metal feedthrough element. In order to tailor a ceramic body of a desired thickness or quality or both the ceramic body can include multiple ceramic layers. The feedthrough element then electrically connects through the ceramic layers of the ceramic body. Such a multilayer feedthrough may be prepared by stacking and laminating ceramic green sheet tapes, providing holes which connect through the laminate of the green sheet tapes, filling a cermet into the holes and sintering the green sheet tapes and the cermet together by firing. Such co-fired technology has been implemented with low temperature co-fired ceramic (LTCC) as well as with high temperature co-fired ceramic (HTCC).

In view of the increasing technical demands of modern cermet-based feed through elements it is often required that the top and the bottoms cermet contacts of a feedthrough element are not congruent when being projected onto a horizontal plane. This is, for example, the case if in a given feedthrough element the cermet contacts at the top surface and the cermet contacts on the bottom surface have to be arranged in a different geometry, particularly in a different density. In case of a feedthrough element that is prepared by the above described LTCC- or HTCC-technique this requires that some sort of horizontal connection between the cermet element of the top green sheet (forming a contact on the top surface) and the cermet element of the bottom green sheet (forming a contact on the top surface) has to be realized by the cermet elements of the internal green sheets to somehow bridge the horizontal offset between the top and the bottom cermet element. In EP 3 041 046 A1 this offset is bridged by proving a conductive material onto the top surface of an intermediate green sheet, wherein the surface area of the conductive material is large enough to ensure an electrical connection between the cermet elements of neighboured green sheets shifted relative to each other in the horizontal plane (see, for example, FIGS. 6-8). One disadvantage of this concept, however, has to be seen that an additional process step is required to provide such a conductive material on the surface of a green sheet element. Furthermore, the provision of a conductive material between the interfaces of two green sheets that are located adjacent to each other may lead to the formation of air gaps between these layers in the final composite and to an increase of the risk of delamination. For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8A illustrates a three-dimensional view of a cermet conductor in another composite according to one embodiment.

FIG. 8B, illustrates a schematic top view of the cermet conductor that is located within the composite illustrated in FIG. 6.

FIGS. 9A-9C illustrate a schematic view of the process according to one embodiment.

FIGS. 10A-10E illustrate a schematic view of the process according to the prior art.

DETAILED DESCRIPTION

Figure 1A:
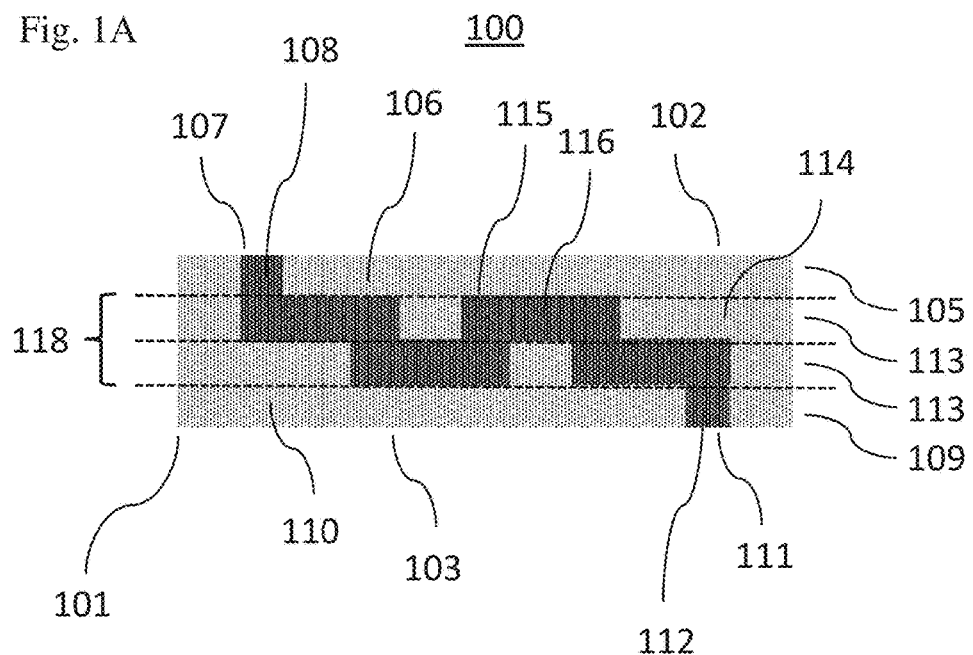
FIG. 1A illustrates a schematic cross sectional side view of a composite according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Generally, embodiments herein at least partly overcome a disadvantage arising from the prior art. One provides a cermet feedthrough based on a cermet that is located in a ceramic multilayer body in which the cermet contacts on the top and the bottom surface are not congruent and in which therefore a horizontal offset between then top and the bottom cermet element has to be bridged by intermediate cermet elements of the cermet feedthrough. Particularly, it should be possible to prepare such a cermet feed through by conventional LTCC- or HTCC-techniques using conventional green sheets without the necessity of applying additional layers between the individual green sheets. Moreover, the cermet feed through should be characterized by an outstanding hermeticity, an outstanding biocompatibility and a high conductivity through the cermet material in the ceramic multilayer body. It is another object of one embodiment to provide a production method for a cermet feedthrough in a ceramic multilayer body which illustrates at least one of the above advantages. It is another object of one embodiment to provide a method of producing such a cermet feedthrough in a ceramic multilayer body, wherein the method results in producing less defect or substandard or both feedthroughs. It is another object of one embodiment to provide a medical implantable electrical device including a cermet feedthrough in a ceramic multilayer body, wherein the feedthrough illustrates at least one of the above advantages. It is another object of one embodiment to provide a pacemaker or a biomonitor or both including a cermet feedthrough in a ceramic multilayer body, wherein the feedthrough illustrates at least one of the above advantages. It is another object of one embodiment to provide a medical implantable electrical device which is characterised by a longer durability period in a body. It is another object of one embodiment to provide a medical implantable electrical device which is less prone to defects when being used in a body. It is another object of one embodiment to provide a medical implantable electrical device which works more reliable when implanted in a body. It is another object of one embodiment to provide a medical implantable electrical device which is less complicated or less expensive or both to produce. It is still another object of one embodiment to provide a pacemaker or a biomonitor or both which is characterised by at least one of the above of a medical implantable electrical device.

A contribution to at least one of the above objects is given by the independent and dependent claims.

A contribution to the solution of at least one of the above objects is made by a composite, including a ceramic body having a first layer surface and a second layer surface and at least one cermet conductor that electrically connects the first layer surface and the second layer surface, wherein the composite has a layer sequence that includes as layers i) a first layer with the first layer surface, wherein the first layer includes a first ceramic, a first hole and a first cermet element included in the first hole, ii) a second layer with the second layer surface, wherein the second layer includes a second ceramic, a second hole and a second cermet element included in the second hole, iii) at least one intermediate layer that is located between the first and the second layer, wherein the at least one intermediate layer includes an intermediate ceramic, at least one intermediate hole and at least one intermediate cermet element included in the at least one intermediate hole, wherein a projection of the cross section of the first hole and a projection of the cross-section of the second hole onto a plane $P_{x,y}$ are arranged offset to each other, wherein the ceramic body includes the ceramic of the individual layers, and wherein the at least one cermet conductor is an electrical connection between the first cermet element and the second cermet element via the at least one intermediate cermet element and wherein the electrical connection is accomplished by an at least partial overlap of cermet elements in layers that are located adjacent to each other.

In the composite according to one embodiment the internal distance between the first and the second cermet (that is, the cermet at the front and the backside of the composite) is not bridged by means of a conductive material that is provided between two green sheet layers as it is done in EP 3 041 046 A1, but is bridged by a conductive path formed by an at least partial overlap between intermediate cermet elements that are located in adjacent intermediate layers, wherein in the area of partial overlap the two neighboured intermediate cermet elements are in a direct contact.

In one embodiment of the composite the layer sequence of the composite includes at least 2 intermediate layers, in one embodiment at least 3, more in one embodiment at least 4, in one embodiment at least 5, in one embodiment at least 6, in one embodiment at least 7, in one embodiment at least 8, in one embodiment at least 9 and in one embodiment at least 10 intermediate layers that are arranged on top of each other forming an interlayer stack that is located between the first and the second layer, wherein the electrical connection within the layer stack is accomplished by an at least partial overlap of the intermediate cermet elements in the intermediate layers that are located adjacent to each other. If 2 or more intermediate layers are present, the electrical connection within the layer stack can be realized in different ways. For example, the cermet conductor can be formed by a straight connection of intermediate cermet elements in intermediate layers that are positioned adjacent to each other. "Straight connection" means that the intermediate cermet elements, at least in a part of the composite, are connected in a consecutive order (with respect to the following intermediate layer) in such a way that the intermediate cermet element of intermediate layer i) is connected with intermediate cermet element of intermediate layer i+1 by partial overlap, which in turn is connected with intermediate cermet element of intermediate layer i+2 by partial overlap and so on, as indicated in the following sequence: intermediate layer

| intermediate layer | | | |
|---|---|---|---|
| i | OOOOOOOO | | |
| i + 1 | | OOOOOOOO | |
| i + 2 | | | OOOOOOOO |

It is, however, also possible to use a connection that at least in a part of the composite is not straight. If, for example, intermediate layers i and i+1 include two intermediate holes, the intermediate cermet elements can be connected in an alternating order (again with respect to the following intermediate layer) in such a way that the first intermediate cermet element of intermediate layer i is connected with the first intermediate cermet element of intermediate layer i+1 by partial overlap, which in turn is connected with the second intermediate cermet element of intermediate layer i by partial overlap, which in turn is connected with the second intermediate cermet element of intermediate layer i+1 by partial and which in turn is connected with intermediate cermet element of intermediate layer i+2 by partial overlap as indicated in the following sequence:

| intermediate layer | | | | | |
|---|---|---|---|---|---|
| i | OOOOOOOO | | OOOOOOOO | | |
| i + 1 | | OOOOOOOO | | OOOOOOOO | |
| i + 2 | | | | | OOOOOOOO |

The composite according to one embodiment is characterized in that a projection of the cross section of the first hole and a projection of the cross section of the second hole onto a plane $P_{x,y}$ are arranged offset to each other. In one embodiment the center of a projection of the cross section of the first hole onto a plane $P_{x,y}$ is located at position $x_1,y_1$, the center of a projection of the cross section of the second hole onto the plane $P_{x,y}$ is located at position $x_2,y_2$, and wherein $x_1 \neq x_2$ and $y_1 = y_2$,
$x_1 \neq x_2$ and $y_1 \neq y_2$, or
$x_1 = x_2$ and $y_1 \neq y_2$.

The center of a projections of the cross section of the first and the second hole onto plane $P_{x,y}$ is a vertical projection, that is, it is a projection in a direction that is vertical to plane $P_{x,y}$.

The projections of the cross sections of the first hole and the second hole onto plane $P_{x,y}$ can thus be arranged offset to each other in x-direction, in y-direction or in both direction. In one embodiment the offset in x-direction is at least 20 μm, in one embodiment at least 200 μm, in one embodiment at least 1000 μm and in one embodiment at least 2500 μm. In another embodiment the offset in y-direction is at least 20 μm, in one embodiment at least 200 μm, in one embodiment at least 1000 μm and in one embodiment at least 2500 μm. In another embodiment the offset in x-direction is at least 20 μm, in one embodiment at least 200 μm, in one embodiment at least 1000 μm and in one embodiment at least 2500 μm and the offset in y-direction is at least 20 μm, in one embodiment at least 200 μm, in one embodiment at least 1000 μm and in one embodiment at least 2500 μm. In another embodiment the distance between the center $x_1,y_1$ and $x_2,y_2$ in plane $P_{x,y}$ is in the range from 20 to 10000 μm, in one embodiment in the range from 200 to 7500 μm, in one embodiment in the range from 1000 to 5000 μm and in one embodiment in the range from 2000 to 4000 μm.

In another embodiment of the composite the first and the second hole can have any shape the person skilled in the art would consider as appropriate to electrically contact the composite at the first and the second surface via the first and the second cermet element included in the first and the second hole, respectively. In one embodiment, the first and the second hole have a symmetric shape. In this context it is preferred in one embodiment that the projection of the first and the second hole onto plane $P_{x,y}$ includes at least one axis of symmetry, in one embodiment two axes of symmetry. In an embodiment of the composite the hole has a diameter in the range from 50 to 800 μm, in one embodiment in the range from 100 to 700 μm, in one embodiment in the range from 150 to 600 μm, in one embodiment in the range from 200 to 500 μm.

In another embodiment of the composite at least one intermediate hole, in one embodiment each intermediate hole in the composite, is an elongated hole. A hole is referred to as an "elongated hole" if a cross section of the projection of the intermediate hole onto the plane $P_{x,y}$ has a length L and a width W, wherein condition L≥2×W, in one embodiment L≥3×W, in one embodiment L≥4×W, in one embodiment L≥5×W and in one embodiment L≥6×W is fulfilled. In this context it is also preferred in one embodiment that intermediate cermet elements have a symmetric shape. In this context it is preferred in one embodiment that the projection of the intermediate hole onto plane $P_{x,y}$ includes at least one axis of symmetry, in one embodiment two axes of symmetry.

In another embodiment of the composite at least one intermediate hole, in one embodiment each intermediate hole in the composite, includes at least at one end of intermediate hole, in one embodiment at both ends, a portion that in a projection onto plane $P_{x,y}$ has a geometrical shape with a width $W_{portion}$, wherein $W_{portion} > W$ and wherein the at least partial overlap of intermediate cermet elements in the intermediate layers that are located adjacent to each other is formed in the area of this portion. Such geometrical shape is advantageous in one embodiment if two neighbored intermediate cermet elements are to be connected by partial overlap which have a width W in the range from 30 to 400 μm and which are not arranged in the same direction (that is, which confine an angle of 180 degrees), but which are arranged obliquely in relation to each other (that is, which confine an angle of less than 180 degrees). In one embodiment, $W_{portion} \geq 1.1 \times W$, in one embodiment $W_{portion} \geq 1.5 \times W$, in one embodiment $W_{portion} \geq 2 \times W$ and in one embodiment $W_{portion} \geq 2.5 \times W$.

The portion at the at least one end of the intermediate hole, in one embodiment at both ends of the intermediate hole, can have any geometrical shape the person skilled in the art would consider as suitable to enlarge the contact area between two neighbored intermediate cermet elements included in these intermediate holes, particular in a situation in which these are arranged obliquely in relation to each other. The portion can, for example, have the shape of a circle, a rectangle or a triangle. In this context it is preferred in one embodiment that the portion has in a projection onto plane $P_{x,y}$, the form of circle having a diameter $W_{portion}$. If the intermediate hole is an elongated hole and if a circular portion the width of which is larger than the diameter of the circular end portions is present at both ends of the elongated hole, the intermediate hole has in a projection onto plane $P_{x,y}$, the form of a dumbbell.

In one embodiment, the area of partial overlap of intermediate cermet elements in intermediate layers that are located adjacent to each other is in the range from 0.002 to 0.8 mm$^2$, in one embodiment 0.005 to 0.5 mm$^2$, in one embodiment 0.03 to 0.3 mm$^2$ and in one embodiment 0.05 to 0.2 mm$^2$.

In another embodiment of the composite at least one intermediate cermet element, in one embodiment each intermediate cermet element in the composite, is an elongated body having a length L in the range from 20 to 10000 μm, in one embodiment in the range from 120 to 9900 μm, in one embodiment in the range from 200 to 7500 μm, in one embodiment in the range from 500 to 5000 μm and in one embodiment in the range from 900 to 3000 μm, and a width W in the range from 10 to 1000 μm, in one embodiment in the range from 40 to 990 μm, in one embodiment in the range from 50 to 750 μm, in one embodiment in the range from 100 to 600 μm and in one embodiment in the range from 300 to 450 μm. The thickness of the intermediate cermet element corresponds to the thickness of the intermediate layer in the holes of which the intermediate cermet element is included.

In another embodiment of the composite at least one layer selected from the group consisting of the first layer, the at least one intermediate layer and the second layer, in one embodiment each of layers of the composite, has a thickness in the range from 75 to 600 μm, in one embodiment in the range from 80 to 550 μm, in one embodiment in the range from 100 to 500 μm, in one embodiment in the range from 200 to 400 μm.

In another embodiment of the composite at least one cermet element selected from the group consisting of the first cermet element, the second cermet element and the at least one intermediate cermet element, in one embodiment each cermet element of the composite, includes.

Pt in the range from 60 wt.-% to the remainder completing the sum of all components to 100 wt.-%, in one embodiment from 65 wt.-% to the remainder completing the sum of all components to 100 wt.-%, in one embodiment from 70 wt.-% to the remainder completing the sum of all components to 100 wt.-%, even in one embodiment from 80 wt.-% to the remainder completing the sum of all components to 100 wt.-%, in one embodiment from 90 wt.-% to the remainder completing the sum of all components to 100 wt.-%; and a) Al$_2$O$_3$ in the range from 0.5 to 25 wt.-%, in one embodiment in the range from 0.5 to 20 wt.-%, in one embodiment in the range from 1 to 15 wt.-%, in one embodiment in the range from 1.1 to 8 wt.-%, in one embodiment in the range from 1.7 to 4.5 30 wt.-%;

each based on the total weight of the cermet element.

According to one embodiment of composite the Pt-content of first and the second cermet element is higher than the Pt-content of the at least one intermediate cermet element. In this context it is preferred in one embodiment that the first and the second cermet element include Pt in the range from 70 wt.-% to the remainder completing the sum of all components to 100 wt.-%, in one embodiment from 80 wt.-% to the remainder completing the sum of all components to 100 wt.-%, in one embodiment from 90 wt.-% to the remainder completing the sum of all components to 100 wt.-%.

In another embodiment of the composite the ceramic body and the conductor are each in one piece.

The electrical resistance of the cermet conductor in the composite according to one embodiment is in the range from 1 to 2000 mΩ, in one embodiment in the range from 5 to 1000 mΩ and in one embodiment in the range from 10 to 300 mΩ.

A contribution to the solution of at least one of the above objects is also made by a process, including as process steps providing a first ceramic green sheet, including a first hole and a first ceramic green sheet surface, filling the first hole with a first cermet precursor composition and drying the first cermet precursor composition;

I) providing at least one intermediate ceramic green sheet, including at least one intermediate hole, filling the at least one intermediate hole with an intermediate cermet precursor composition and drying the intermediate cermet precursor composition;

II) providing a second ceramic green sheet, including a second hole and a second ceramic green sheet surface, filling the second hole with a second cermet precursor composition and drying the second cermet precursor composition;

III) arranging the first ceramic green sheet, the at least one intermediate ceramic green sheet and the second ceramic green sheet in a sequence such that the at least one intermediate ceramic green sheet is located between the first and the second ceramic green sheet;

IV) firing the sequence of ceramic green sheets thereby obtaining a composite including a ceramic body and a cermet conductor;

wherein the holes in the individual green sheets are located and formed in such a way that a projection of the cross section of the first hole and a projection of the cross-section of the second hole onto a plane $P_{x,y}$ are arranged offset to each other, and in the ceramic body the cermet conductor is formed by an electrical connection between the first cermet element that in process step V) is formed in the first hole and the second cermet element that in process step V) is formed in the second hole via the at least one intermediate cermet element that in process step V) is formed in the at least one intermediate hole and wherein the electrical connection is accomplished by an at least partial overlap of the cermet elements in the layers that are located adjacent to each other.

For the person skilled in that are it is evident that process steps I), II) and III) can be performed in any order (that is, it is not relevant which of the ceramic green sheets is provided first).

In another embodiment of the process, in process step II) at least 2, in one embodiment at least 3, in one embodiment at least 4, in one embodiment at least 5, in one embodiment at least 6, in one embodiment at least 7, in one embodiment at least 8, in one embodiment at least 9 and in one embodiment at least 10 intermediate ceramic green sheets are provided, wherein in process step IV) the at least 2, in one embodiment the at least 3, in one embodiment the at least 4, in one embodiment the at least 5, in one embodiment the at least 6, in one embodiment the at least 7, in one embodiment the at least 8, in one embodiment the at least 9 and in one embodiment the at least 10 intermediate ceramic green sheets are arranged on top of each other forming an intermediate ceramic green sheet stack that is located between the first and the second ceramic green sheet, wherein the electrical connection within the intermediate layer stack that in process step V) is derived from the intermediate ceramic green sheet stack is accomplished by an at least partial overlap of the intermediate cermet elements in intermediate layers that are located adjacent to each other.

In another embodiment of the process the intermediate holes in the individual intermediate ceramic green sheets are located and formed in such a way that, upon arrangement of the ceramic green sheets in process step IV) and firing in process step V), a straight connection of intermediate cermets elements or a non-straight connection of intermediate cermets elements results, as described above in connection with the composite according to one embodiment.

According to one embodiment of the process the first and the second hole in the first and the second ceramic green sheet are located and formed in such a way that, upon arrangement of the ceramic green sheets in process step IV) and firing in process step V), the center of a projection of the cross section of the first hole onto a plane $P_{x,y}$ is located at position $x_1,y_1$, the center of a projection of the cross section of the second hole onto the plane $P_{x,y}$ is located at position $x_2,y_2$, and wherein
$x_1 \neq x_2$ and $y_1 = y_2$,
$x_1 \neq x_2$ and $y_1 \neq y_2$, or
$x_1 = x_2$ and $y_1 \neq y_2$.

According to another embodiment of the process the projections of the cross sections of the first hole and the second hole onto plane $P_{x,y}$ can this be arranged offset to each other in x-direction, in y-direction or in both direction. In one embodiment the offset in x-direction is at least 20 μm, in one embodiment at least 200 μm, in one embodiment at least 1000 μm and in one embodiment at least 2500 μm. In another embodiment the offset in y-direction is at least 20 μm, in one embodiment at least 200 μm, in one embodiment at least 1000 μm and in one embodiment at least 2500 μm. In another embodiment the offset in x-direction is at least 20 μm, in one embodiment at least 200 μm, in one embodiment at least 1000 μm and in one embodiment at least 2500 μm and the offset in y-direction is at least 20 μm, in one embodiment at least 100 μm, in one embodiment at least 1000 μm and in one embodiment at least 2500 μm. In another embodiment the distance between the center $x_1,y_1$ and $x_2,y_2$ in plane $P_{x,y}$ is in the range from 20 to 10000 μm, in one embodiment in the range from 200 to 7500 μm, in one embodiment in the range from 1000 to 5000 μm and in one embodiment in the range from 2000 to 4000 μm.

According to another embodiment of the process at least one intermediate hole, in one embodiment each intermediate hole of the intermediate ceramic green sheets that are used in the process, is as defined above in connection with the intermediate holes in the composite according to one embodiment, and at least one intermediate cermet element, in one embodiment each intermediate cermet element in the composite obtained after process step V), is as defined above in connection with the intermediate cermet element in the composite according to one embodiment.

According to another embodiment of the at least one cermet precursor composition selected from the group consisting of the first cermet precursor composition, the second cermet precursor composition and the intermediate cermet precursor composition, in one embodiment each of these precursor compositions, includes A) Pt in the range from 60 wt.-% to the remainder completing the sum of all components to 100 wt.-%, in one embodiment in the range from 65 wt.-% to the remainder completing the sum of all components to 100 wt.-%, in one embodiment in the range from 70 wt.-% to the remainder completing the sum of all components to 100 wt.-%, in one embodiment in the range from 80 wt.-% to the remainder completing the sum of all components to 100 wt.-%, B) $Al_2O_3$ in the range from 0.5 to 25 wt.-%, in one embodiment in the range from 0.5 to 20 wt.-%, in one embodiment in the range from 1 to 15 wt.-%, in one embodiment in the range from 1.1 to 8 wt.-%, in one embodiment in the range from 1.7 to 4.5 wt.-%, C) a vehicle in the range from 8 to 30 wt.-%, in one embodiment in the range from 9 to 28 wt.-%, in one embodiment in the range from 9 to 22 wt.-%, in one embodiment in the range from 9 to 12 wt.-%, each based on the total weight of the composition.

As stated above in connection with a particular embodiment of composite according to one embodiment the Pt-content of the first and the second cermet element is higher than the Pt-content of the at least one intermediate cermet element. In this context it is preferred in one embodiment that the first cermet precursor composition and the second cermet precursor composition include Pt in the range from 70 wt.-% to the remainder completing the sum of all components to 100 wt.-%, in one embodiment from 80 wt.-% to the remainder completing the sum of all components to 100 wt.-%, in one embodiment from 90 wt.-% to the remainder completing the sum of all components to 100 wt.-%.

According to another embodiment of the process arranging of the ceramic green sheets in process step IV) is performed by laminating. In one embodiment laminating of ceramic green sheets is accomplished by pressing the green sheets together in the order defined in process step IV) using a pressure in the range from 100 to 500 bar, in one embodiment in the range from 150 to 450 bar, in one embodiment in the range from 200 to 400 bar, in one embodiment in the range from 300 to 400 bar.

A contribution to the solution of at least one of the above objects is also made by a composite obtainable by the process according to one embodiment.

A contribution to the solution of at least one of the above objects is also made by device including a housing, an inner volume, an outer volume, and the composite according to one embodiment or a composite obtainable by the process according to one embodiment, wherein the housing α1) encloses the inner volume,
α2) separates the inner volume from the outer volume, and
α3) includes an aperture;
wherein the aperture frames the composite.

A device according to one embodiment is an electrical device. In one embodiment electrical device is an implantable electrical device. In one embodiment implantable electrical device is a medical implantable electrical device. In one embodiment the cermet element or at least one further cermet element or both electrically connects the inner volume to the outer volume. In one embodiment, the cermet element and each further cermet element electrically connect the inner volume to the outer volume.

In an embodiment, the device is one selected from the group consisting of a pacemaker, a neuro-stimulator, a measuring device and a defibrillator or a combination of at least two thereof. In one embodiment. a pacemaker is one selected from the group consisting of a bladder pacemaker, a breath pacemaker, an intestinal pacemaker, a diaphragm pacemaker, a cerebral pacemaker and a cardiac pacemaker or a combination of at least two thereof. In one embodiment, a pacemaker is a cardiac pacemaker. In one embodiment, a measuring device is a biomonitor. In one embodiment, a device is a biomonitor.

Hole

The term "hole" used in this paragraph refers to the first hole, the second hole or the intermediate hole, each according to one embodiment. In one embodiment hole includes a front face in a first surface of a given layer; an end face in a second surface of a given layer; and a lateral surface connecting the front face to the end face, wherein the lateral surface is a material surface within the ceramic of the given layer. The hole extends through the ceramic material of the given layer. The front face and the end face and a transversal cross section of the lateral surface of the first and the second hole can have any shape of a geometrical surface that seems applicable according to one embodiment to the skilled person. Therein, the front face, the end face and the cross section of the lateral surface of the first and the second hole have to be shaped to be able to accommodate a male connector end of a lead. In one embodiment front face is cyclic or rectangular or both. In one embodiment end face is cyclic or rectangular or both. In one embodiment lateral surface of the hole is at least partly cylindrical. Another in one embodiment lateral surface of the hole is prism-shaped or tortuous or both.

Layer

The term "layer" used in this paragraph includes any layer according to one embodiment. For the use throughout this document a layer superimposes a layer surface of another layer if the layer follows the other layer in the direction which the layer surface faces. A layer which superimposes a layer surface may be bonded to the layer surface. In one embodiment bond is a physical bond or a chemical bond or both. A layer which superimposes a layer surface may follow the layer surfaces directly or there may be additional layers, substances or objects between the layer and the layer surface which is superimposed by the layer. Any layer may include sublayers.

Cermet

According to one embodiment a cermet is a composite material, including at least one ceramic component in at least one metallic matrix; or a composite material, including at least one metallic component in a least one ceramic matrix; or both. At least one ceramic powder and at least one metallic powder can for example be applied for preparing a cermet, wherein to at least one of the powders for example a binder can be added and optionally at least one surfactant. The ceramic powder/the ceramic powders of the cermet in one embodiment have an average grain size of less than 10 µm, in one embodiment less than 5 µm, in one embodiment less than 3 µm. In some cases the ceramic powder of the cermet has an average particle size of at least 15 µm. The metallic powder/the metallic powders of the cermet in one embodiment have an average grain size of less than 15 µm, in one embodiment less than 10 µm, in one embodiment less than 5 µm. Therein, the average grain size is particularly the median value or the $D_{50}$. The $D_{50}$ gives the value, at which 50% of the grains of the ceramic powder and/or the metallic powder are smaller than the $D_{50}$. In one embodiment cermet is characterised by a high specific conductivity, which is in one embodiment at least 1 S/m, in one embodiment at least $10^3$ S/m, in one embodiment at least $10^4$ S/m, in one embodiment at least 10'S/m, and in one embodiment at least $10^6$ S/m. The at least one ceramic component of the cermet according to one embodiment includes in one embodiment a ceramic according to one embodiment. The at least one metallic component of the cermet according to one embodiment includes one selected from the group consisting of platinum, iridium, niobium, palladium, iron, stainless steel, a cobalt-chromium-alloy, molybdenum, tantalum, tungsten, titanium, cobalt and zirconium or a combination of at least two thereof. Therein, a preferred combination in one embodiment is an alloy. In one embodiment stainless steel is stainless steel 316L. Generally, the cermet becomes electrically conductive if the metal content of the cermet is above the so called percolation threshold, at which metal particles in the sintered cermet are at least partly connected to each other in such a way that electrical charges can be transported via conduction. Therefore, the metal content of the cermet should according to experience depending on the choice of materials be at least 25 vol.-%, in one embodiment at least 32 vol.-%, in one embodiment at least 38 vol.-%, each based on the total volume of the cermet.

Ceramic

A ceramic according to one embodiment can be any ceramic the skilled person deems applicable to the embodiment. The ceramic is in one embodiment selected from the group consisting of an oxide ceramic, a silicate ceramic and a non-oxide ceramic or a combination of at least two thereof.

The oxide ceramic includes in one embodiment a metal oxide or a metalloid oxide or both. A metal of the metal oxide is in one embodiment selected from the group consisting of aluminium, beryllium, barium, calcium, magnesium, sodium, potassium, iron, zirconium, titanium, or a combination of at least two thereof. In one embodiment metal oxide is selected from the group consisting of aluminium oxide ($Al_2O_3$); magnesium oxide (MgO); zirconium oxide (ZrOz); yttrium oxide ($Y_2O_3$); aluminium titanate ($Al_2TiO_5$); a piezoceramic as for example lead-zirconate ($PbZrO_3$), lead-titanate ($PbTiO_3$) and lead-zirconate-titanate (PZT); or a combination of at least two thereof. In one embodiment, a metalloid of the metalloid oxide is selected from the group consisting of boron, silicon, arsenic, tellurium, or a combination of at least two thereof. In one embodiment, oxide ceramic includes one selected from the group consisting of aluminium oxide toughened with zirconium oxide enhanced (ZTA-Zirconia Toughened Aluminium-$Al_2O_3$/$ZrO_2$), zirconium oxide toughened with yttrium (Y-TZP), barium(Zr, Ti)oxide, barium(Ce, Ti)oxide or a combination of at least two thereof.

The silicate ceramic is in one embodiment selected from the group consisting of a steatite ($Mg_3[Si_4O_{10}(OH)_2]$), a cordierite (Mg, $Fe^{2+})_2(Al_2Si)[Al_2Si_4O_{18}]$), a mullite ($Al_2Al_{2+2x}Si_{2-2x}O_{10-x}$ with x=oxide defects per unit cell), a feldspar ($Ba,Ca,Na,K,NH_4)(Al,B,Si)_4O_8$) or a combination of at least two thereof.

The non-oxide ceramic in one embodiment includes a carbide or a nitride or both. In one embodiment, carbide is one selected from the group consisting of silicon carbide (SiC), boron carbide ($B_4C$), titanium carbide (TiC), tungsten carbide, cementite ($Fe_3C$) or a combination of at least two thereof. In one embodiment, nitride is one selected from the group consisting of silicon nitride ($Si_3N_4$), aluminium nitride (AlN), titanium nitride (TiN), silicon aluminium oxinitride (SIALON) or a combination of at least two thereof. In one embodiment non-oxide ceramic is sodium-potassium-niobate.

Width and Length

The terms "width" (W) and "length" (L) are used herein to define the dimension of the projection of a given intermediate hole in plane $P_{x,y}$. This projection is characterized by a first dimension $D_1$ and a second dimension $D_2$, the direction of first dimension $D_1$ being perpendicular to the direction the second dimension $D_2$, wherein, if $D_1<D_2$, $D_1$ corresponds to the width W and $D_2$ corresponds to the length L (see also FIG. 5). In case of a cermet element having a projection onto plane $P_{x,y}$ the form of a square, the length L is identical to the width L ($D_1=D_2$). If the width W of the projection of a given intermediate cermet onto plane $P_{x,y}$ varies along the length L (as in the case of a projection of the intermediate hole onto plane $P_{x,y}$ in the form of a dumbbell as illustrated in FIG. 7), the width W corresponds to the maximum value of the width along the length of the projection of the intermediate hole. Thus, if the intermediate cermet element is, for example, in the form of a dumbbell, the diameter of the circles (=$W_{portion}$) at the two ends of the dumbbell corresponds to the value for W that has to satisfy the condition L≥2×W according to one embodiment of the composite.

Center

The term "center" as used herein, particularly in connection with the wording "center of a projection of a cross section", defines the balance point S of a two-dimensional area A. The balance point S of a two-dimensional area A can be mathematically determined by dividing the area A in partial areas ΔA, determining the partial balance point ST in these partial areas ΔA and by applying the principle of angular momentum to determine the balance point S of the total area A. If, as in the composite according to one embodiment, the intermediate hole is a symmetrical hole having at least two axes of symmetry in the plane $P_{x,y}$, the center of this symmetrical hole is defined by the point of intersection of these two axes of symmetry.

Drying

In one embodiment drying includes a peak temperature in the range from 50 to 500° C., in one embodiment in the range from 70 to 400° C., in one embodiment in the range from 100 to 300° C., in one embodiment in the range from 100 to 200° C. In one embodiment drying is performed for at least 3 minutes, in one embodiment for at least 4 minutes, in one embodiment for at least 5 minutes, in one embodiment for at least 7 minutes, in one embodiment for at least 10 minutes.

Firing

Firing can be performed in any oven the skilled person deems appropriate for firing the respective green sheet. In one embodiment firing is performed in a box oven. In one embodiment firing includes a peak temperature in the range from 1000 to 2000° C., in one embodiment in the range from 1250 to 1900° C., in one embodiment in the range from 1510 to 1650° C. In one embodiment firing includes keeping a peak temperature constant for a duration in the range from 0.3 to 10 hours, in one embodiment in the range from 0.5 to 7 hours, in one embodiment in the range from 1 to 5 hours.

Test Methods

The following test methods are used in one embodiment. In absence of a test method, the ISO test method for the feature to be measured being closest to the earliest filing date of the present application applies. In absence of distinct measuring conditions, standard ambient temperature and pressure (SATP) as a temperature of 298.15 K (25° C., 77° F.) and an absolute pressure of 100 kPa (14.504 psi, 0.986 atm) apply.

Layer Thickness

The layer thickness is measured using a micrometer screw gauge. Therein, the measuring spindle of the micrometer is screwed slowly towards the probe applying the ratchet. The ratchet limits the force applied by the measuring spindle to the probe to 5 to 10 N. For the measurement the micrometer is fixed to a tripod in order to prevent distortions due to warmth from a hand.

Dimension of Holes

The dimension of holes (W, $W_{portion}$, L) can be measured using an optical microscope.

EXAMPLES

Embodiments are now explained in more detail by examples and drawings given by way of example, wherein the examples and drawings do not limit the invention.

Paste Recipe 60 g of Pt powder were mixed with 24 g of aluminium oxide powder and a cellulose solvent based organic vehicle and homogenised with a three roll mill. The pastes exhibited a rheology that was suitable for stencil printing.

Ceramic Green Sheet Preparation

Figure 10D:
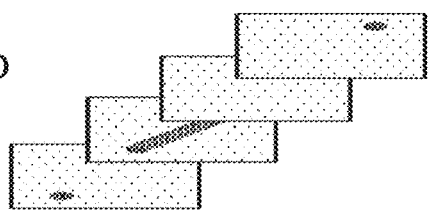
Figure 10E:

A ceramic green tape was used for the preparation of the individual ceramic green sheets. The ceramic tape used was a 99.7% high purity alumina tape. The green tape thickness was 400 μm. Green tape samples were cut to 90 mm×90 mm squares. About circular holes of 400 μm diameter were punched into the green tape used for the first and the second ceramic green sheet using a 400 μm diameter mechanical punch in an automatic puncher machine (see, for example, green sheets 1 and 4 in FIG. 9 or green sheets 1, 2, 3 and 4 in FIG. 10). Holes in the form of a dumbbell having a length of 1200 μm, a width W of 300 μm and a width at end portions $W_{portion}$ of 400 μm were punched in the green sheets used for the formation of the intermediate layers (see, for example, green sheets 2 and 3 in FIG. 9).

Filling

The filling of the holes was performed using a stencil with a specific pattern on an EKRA Microtronic II printer (type M2H). The stencil thickness was 100 μm. The stencil openings had the same dimensions and location as the holes punched through the ceramic green tape. The squeegee cycle was set so that cermet material would be deposited in both the forward and backward squeegee movements. The filling step was repeated a minimum of 3 times until a satisfactory amount of material was deposited in all holes.

Drying 10 minutes after printing the samples were placed in a drying apparatus and dried at 150° C. for 10 minutes.

Laminating 3 to 7 layers of green tape with the holes filled according to the above process were stacked using a metal aligning tool and isostatically pressed under 350 bar of pressure in an oil bath at elevated temperature in order to achieve the desired component thickness.

Firing

The resulting laminate of green tapes was fired in a high temperature box oven capable of providing a peak temperature of 1750° C. with a firing chamber of size 200 mm×250 mm×200 mm. The firing took place under normal atmosphere conditions. The temperature was increased to 450° C. in order to burn away organic components remaining in the green laminate. Subsequently, the temperature was increased to a peak temperature in the range from 1510 to 1650° C. and then kept at that temperature for a period of time in the range from 1 to 5 hours. Subsequently, the temperature was decreased to room temperature.

Post-Firing Processing

After the end of the firing process the plug was removed and the samples were ground and cut to the desired dimensions by laser cutting.

Figure 1B:
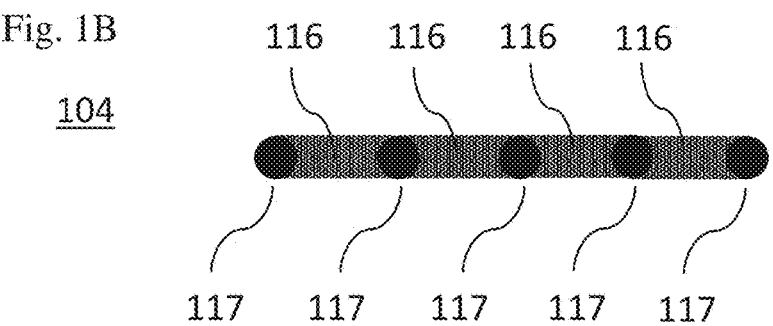
FIG. 1B illustrates a schematic top view of the cermet conductor that is located within the composite illustrated in FIG. 4.
Figure 2:
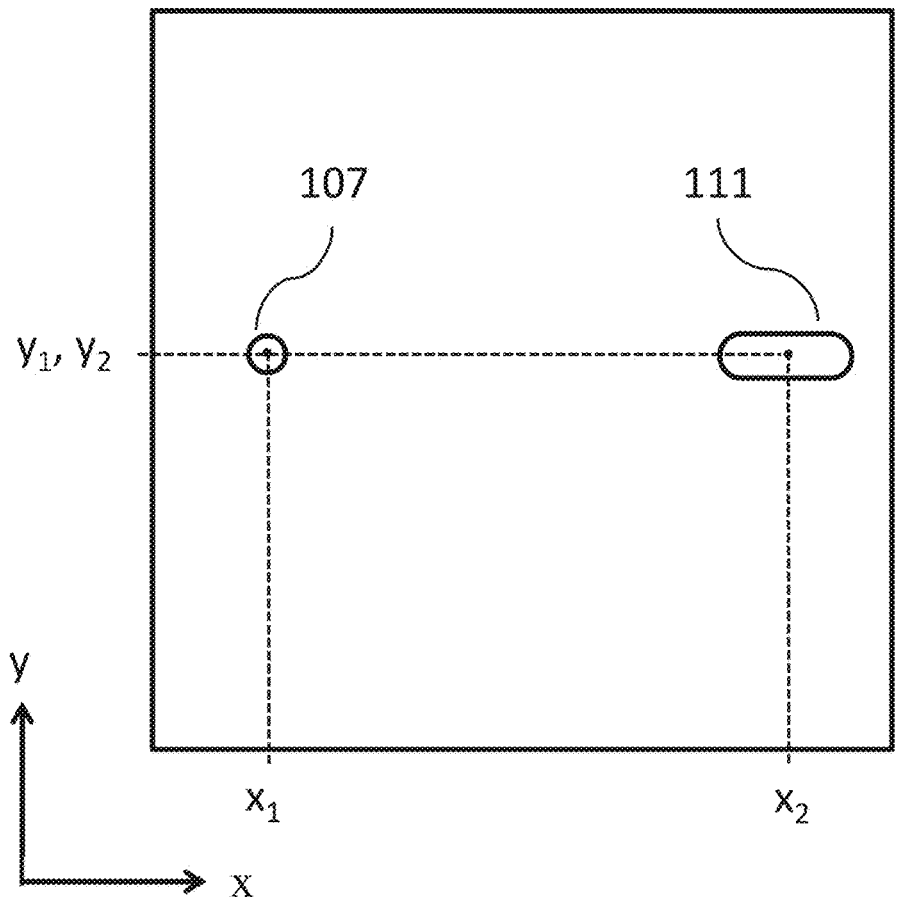
FIG. 2 illustrates a schematic top view of composite according to one embodiment only illustrating the location of the first and the second cermet element in plane $P_{xy}$, in which the first and the second cermet element are arranged offset to each other in x-direction.
Figure 3:
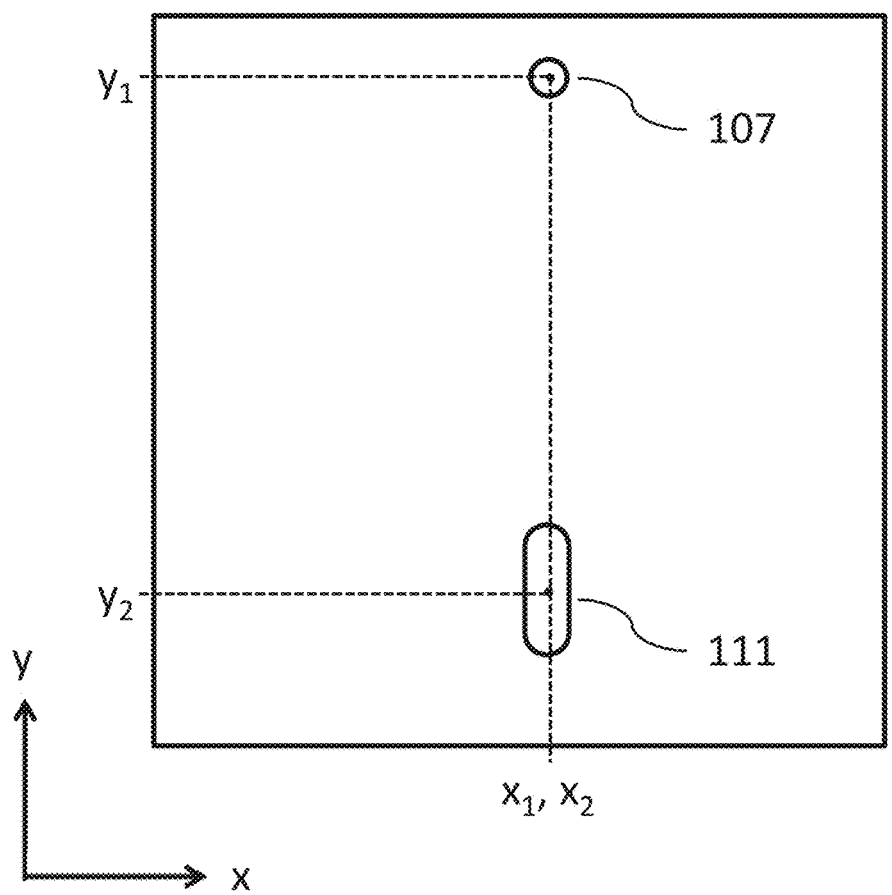
FIG. 3 illustrates a schematic top view of composite according to one embodiment, in which the first and the second cermet element are arranged offset to each other in y-direction.
Figure 4:
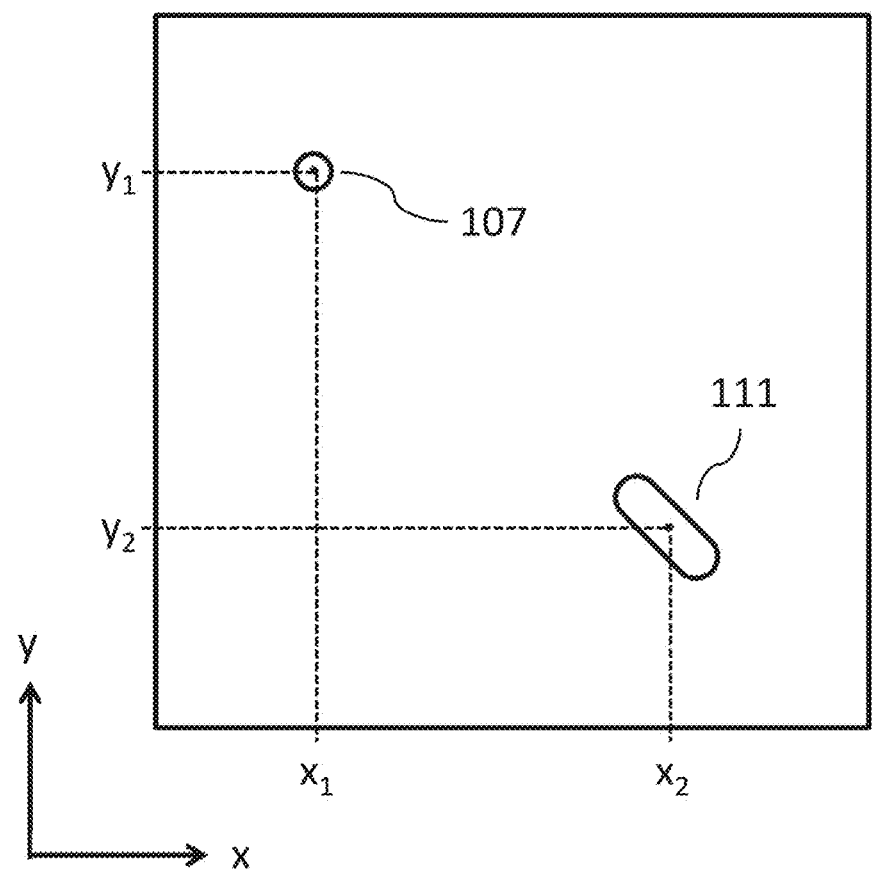
FIG. 4 illustrates a schematic top view of composite according to one embodiment, in which the first and the second cermet element are arranged offset to each other in x- and in y-direction.

FIG. 1A illustrates a schematic cross sectional side view of a composite 100 according to one embodiment. The composite 100 includes a ceramic body 101 having a first layer surface 102 and a the second layer surface 103 and at least one cermet conductor 104 that electrically connects the first layer surface 102 and the second layer surface 103. The composite 100 has a layer sequence that includes as layers a first layer 105 with the first layer surface 102, wherein the first layer 105 includes a first ceramic 106, a first hole 107 and a first cermet element 108 included in the first hole 107, a second layer 109 with the second layer surface 103, wherein the second layer 109 includes a second ceramic 110, a second hole 111 and a second cermet element 112 included in the second hole 111, and at least one intermediate layer 113 that is located between the first and the second layer 105,109, wherein the at least one intermediate layer 113 includes an intermediate ceramic 114, at least one intermediate hole 115 and at least one intermediate cermet element 116 included in the at least one intermediate hole 115. The exemplary composite illustrated in FIG. 1A includes two intermediate layers 113 that are arranged on top of each other forming an interlayer stack 118 that is located between the first and the second layer 105,109. In the composite according to one embodiment, a projection of the cross section of the first hole 107 and a projection of the cross section of the second hole 111 onto a plane $P_{x,y}$ are arranged offset to each other, as also illustrated in FIGS. 2, 3 and 4. The ceramic body 101 includes the ceramic 106,110,114 of the individual layers 105,109,113. The at least one cermet conductor 104, that in FIG. 1B is illustrated in a top view, is an electrical connection between the first cermet element 108 and the second cermet element 112 via the at least one intermediate cermet element 116, wherein the electrical connection is accomplished by an at least partial overlap 117 of cermet elements 108,112,116 in layers 105,109,113 that are located adjacent to each other. In the exemplary composite illustrated in FIG. 1A the electrical connection within the layer stack 118 is accomplished by an at least partial overlap 117 of the intermediate cermet elements 116 the two intermediate layers 113 that are located adjacent to each other. The first, the second and the intermediate ceramic 106,110,114 are $Al_2O_3$. Cermet elements 108, 112 and 116 include a cermet, wherein the cermet includes 97 wt.-% Pt and 3 wt.-% $Al_2O_3$, each based on the total weight of the cermet element. As illustrated in FIG. 1B, the offset between the first and the second cermet element 108,112 is internally (that is, within the composite) bridged by a partial overlap 117 of the intermediate cermet elements.

FIGS. 2, 3 and 4 are a schematic top view of composite according to one embodiment only illustrating the location of the first and the second hole 107,111 in a projection onto plane $P_{x,y}$. These figures illustrate possible offset arrangements of the first and the second hole 107,111 in the composite. In FIG. 2 an arrangement is illustrated in which the first and the second hole 107,111 are arranged offset to each other in x-direction, FIG. 3 illustrates an arrangement in which the first and the second hole 107,111 are arranged offset to each other in y-direction and FIG. 4 illustrates an arrangement in which the first and the second hole 107,111 are arranged offset to each other in x- and in y-direction.

Figure 5:
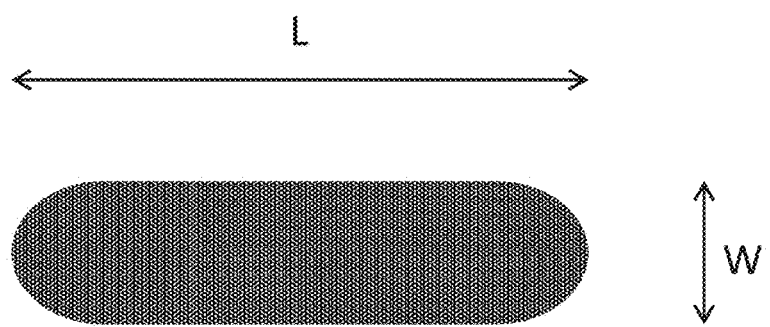
FIG. 5 illustrates a schematic top view of a projection of an intermediate hole onto plane $P_{x,y}$.

FIG. 5 a schematic top view of a projection of an intermediate hole onto plane $P_{x,y}$. As illustrated in this, the intermediate hole in one embodiment is an elongated hole, in one embodiment a hole having a length L and a width W, wherein L≥2×W.

Figure 6:
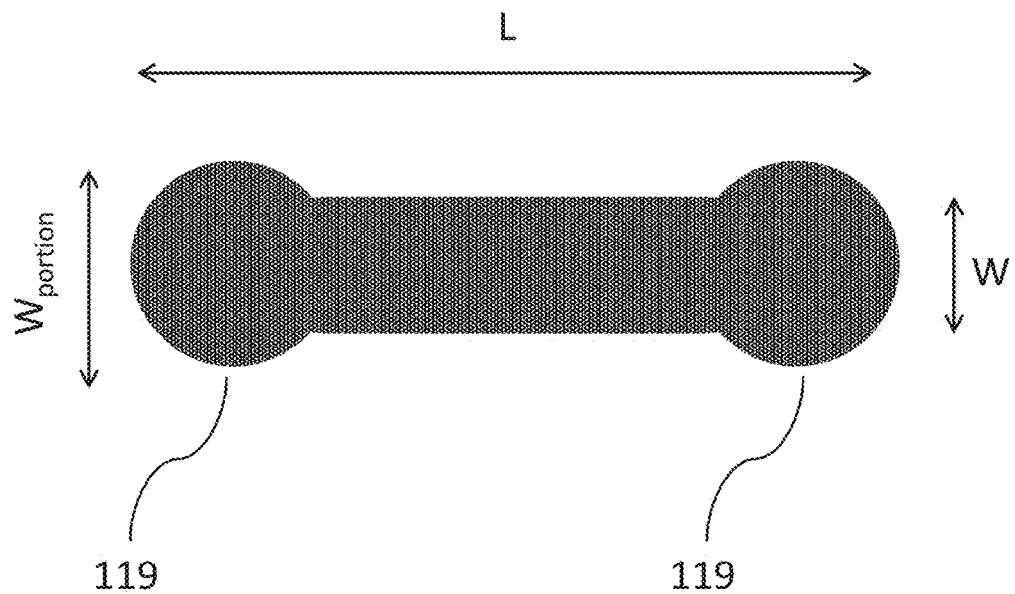
FIG. 6 illustrates a schematic top view of a projection of an intermediate hole onto plane $P_{x,y}$, the intermediate hole having the form of a dumbbell.

FIG. 6 illustrates a schematic top view of a projection of an intermediate hole 115 onto plane $P_{x,y}$, that is advantageous in one embodiment to connect intermediate cermet elements 116 in adjacent layers, wherein these intermediate cermet elements 116 confine an angle of less than 180 degree. Such an intermediate hole 115 includes, at least at one end of the at least one intermediate hole 115, a portion 119 that in a projection onto plane $P_{x,y}$ has a geometrical shape with a width $W_{portion}$, wherein $W_{portion}$>W and wherein the at least partial overlap 117 of cermet elements 108,112,116 in the layers 105,109,113 that are located adjacent to each other is formed in the area of this portion 119. As illustrated in the particular embodiment of FIG. 6, the projection of an intermediate hole onto plane $P_{x,y}$ can have the form of a dumbbell having the length L, the width W in the middle portion of the dumbbell and a width $W_{portion}$ that corresponds to the diameter of the circular shaped end portions 119.

Figure 7A:
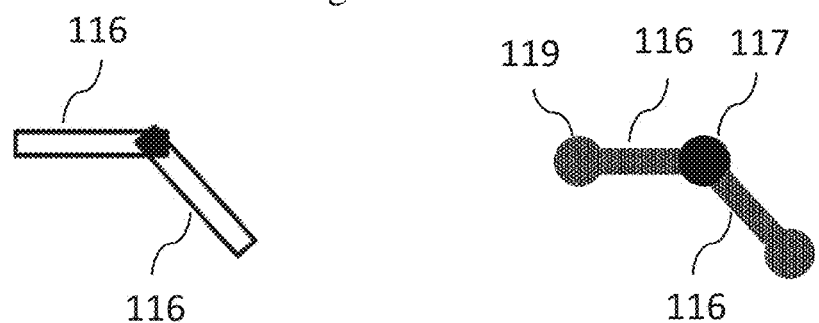
FIGS. 7A-7C illustrate a schematic view of arrangements of adjacent intermediate cermet with an without an enlargement at the overlapping area.
Figure 7B:
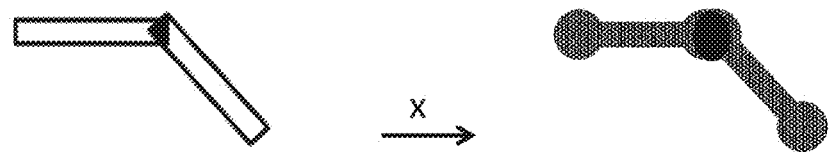
Figure 7C:
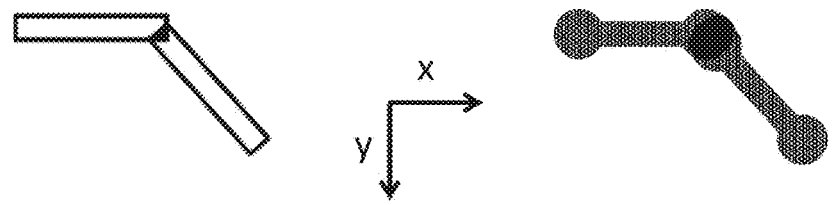

FIGS. 7A-C illustrate a schematic view of arrangements of adjacent intermediate cermet elements 116 without (left) and with (right) an enlargement at the overlapping area in a projection onto plane $P_{x,y}$. In the embodiment illustrated in FIGS. 7A-C the intermediate cermet elements 116 are arranged obliquely in relation to each other (that is, they confine an angle of less than 180 degrees). As illustrated in FIG. 7A, a sufficient overlap between two intermediate cermet elements 116 can also be achieved if the end portions of the intermediate cermet elements 116 do not include any enlargement of the overlapping area 117 (for example in the form of the circular portions 119 illustrated in the dumbbell of FIG. 6, provided that there is an optimum positioning of the two intermediate ceramic green above each other. However, when preparing ceramic composites by means of the LTCC- or HTCC-technology, that is, by a process in which several ceramic green sheets including holes filled with a dried cermet paste are stacked on top of each other, such an optimum positioning is, mainly due to production-related issues, not always guaranteed. As illustrated in FIGS. 7B and 7C, when positioning two ceramic green sheets on top of each other a shift in one direction (see FIG. 7B) illustrating a shift in the x-direction) or in two directions (see FIG. 7C) illustrating a shift in both, the x- and the y-direction) can be observed. In such a case, however, the partial overlap 117 between two neighbored intermediate cermet elements 116 is significantly reduced, as illustrated on the left of FIGS. 7B and 7C. An enlargement of the contact area 117, however, ensures an overlap that leads to a sufficient electrical contact between the intermediate cermet elements 116 (as illustrated on the right of FIGS. 7B and 7C).

FIG. 8A illustrates a three-dimensional view of a cermet conductor 104 in another composite 100 according to one embodiment. The cermet conductor 104 includes a first cermet element 108 having a circular cross-section, and a second cermet element 112 having a cross-section in the form of an elongated hole. As illustrated in FIG. 8B, in the cermet conductor 104 the first cermet element 108 and the second cermet element 112 are arranged offset to each other (both, in the x- and the y-direction). The cermet conductor 104 includes four intermediate cermet elements 116, wherein the first intermediate cermet element 116 (from the left) is connected by partial overlap 117 with the first cermet element 108 and the last cermet element is connected by partial overlap 117 with the second cermet element 112. The second and the third intermediate cermet element 116 confine an angle of less than 180 degree. In such a configuration it is advantageous in one embodiment if the overlapping area 117 includes an enlargement of the contact area in form of a portion 119 to ensure a sufficient electrical contact between these intermediate cermet elements 116.

FIGS. 9A-C illustrate a schematic view of the process according to one embodiment. As illustrated in FIG. 9A, in process step I) a first ceramic green sheet is provided that includes a first hole and a first ceramic green sheet surface. The first hole has a diameter of 400 μm and is filled with a first cermet precursor composition, followed by drying the first cermet precursor composition to obtain the first ceramic green sheet (green sheet 1 in FIG. 9A). The ceramic of the first ceramic green sheet is $Al_2O_3$ and the first cermet precursor composition includes 60 g of Pt powder, 24 g of aluminium oxide powder and a cellulose solvent based organic vehicle. In process step II) two intermediate ceramic green sheets are provided that include an intermediate hole in the form of a dumbbell. The intermediate hole as a length of 1200 μm, a width W of 300 μm and a width at end portions $W_{portion}$ of 400 μm and is filled with an intermediate cermet precursor composition, followed by drying the intermediate cermet precursor composition to obtain the two intermediate ceramic green sheets (green sheets 2 and 3 FIG. 9A). The ceramic of the intermediate ceramic green sheets is $Al_2O_3$ and the intermediate cermet precursor composition includes 60 g of Pt powder, 24 g of aluminium oxide powder and a cellulose solvent based organic vehicle. In process step III) a second ceramic green sheet is provided that includes a second hole and a second ceramic green sheet surface. The second hole has a diameter of 400 μm and is filled with a second cermet precursor composition, followed by drying the first cermet precursor composition to obtain the first ceramic green sheet (green sheet 4 in FIG. 9A). The ceramic of the second ceramic green sheet is $Al_2O_3$ and the second cermet precursor composition includes 60 g of Pt powder, 24 g of aluminium oxide powder and a cellulose solvent based organic vehicle. Process steps I), II) and III) can be performed in any order. As illustrated in FIG. 9B in process step IV) the first ceramic green sheet, the two intermediate ceramic green sheets and the second ceramic green sheet are arranged in a sequence such that the two intermediate ceramic green sheets are located between the first and the second ceramic green sheet. In this process step arranging the green sheets is accomplished by lamination as described above in the experimental section. In process step V) the sequence of ceramic green sheets is fired as described above in the experimental section, thereby obtaining a composite including a ceramic body and a cermet conductor. A cross sectional side view of the composite obtained in process step V) is illustrated in FIG. 9C.

FIGS. 10A-E illustrates a schematic view of the process disclosed in EP 3 041 046 A1. In this process the offset between the first and the second cermet element is bridged by proving a conductive material interlayer 120 between two intermediate green sheets in which the cermet elements are not congruent (see FIG. 10C). The area of this conductive material layer 120 is large enough to ensure an electrical connection between the cermet elements of neighboured green sheets shifted relative to each other in the horizontal plane. When following the approach of the process disclosed in EP 3 041 046 A1, an increased risk of delamination has been observed, which leads to an increased risk of device failure. Also, these composites are characterized by a worse signal-to-noise ratio and a lower electrical performance compared to the device obtained by the process according to one embodiment and illustrated in FIGS. 9A-C.

Figure 11:
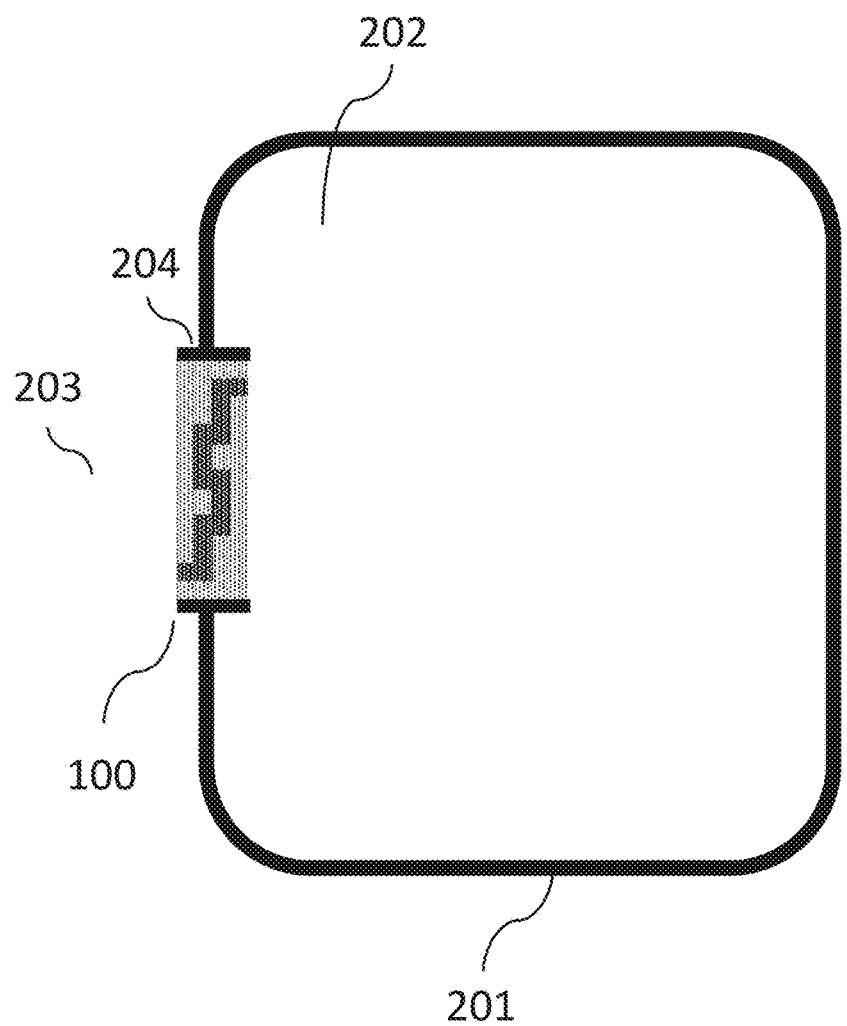
FIG. 11 illustrates a schematic cross sectional side view of a device according to one embodiment.

FIG. 11 illustrates a schematic cross sectional side view of a device 200 according to one embodiment. The device 200 includes a hollow body 201, here a metal housing 201; an inner volume 202; and an outer volume 203; and the composite 100 of FIG. 1A. Therein, the metal housing 201 is made of a titanium alloy which is biocompatible and suitable for medical applications. Furthermore, the metal housing 201 encloses the inner volume 202, separates the inner volume 202 from the outer volume 203, and includes an aperture 204. The aperture 204 frames the composite 100. The connection between the aperture 204 and the composite 100 is sealed by soldering. The device 200 is a biomonitor.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:
1. A composite, comprising:
a ceramic body having a first layer surface and a second layer surface and
at least one cermet conductor that electrically connects the first layer surface and the second layer surface,
wherein the composite has a layer sequence that comprises as layers:
  i) a first layer with the first layer surface, wherein the first layer comprises a first ceramic, a first hole and a first cermet element comprised in the first hole;
  ii) a second layer with the second layer surface, wherein the second layer comprises a second ceramic, a second hole and a second cermet element comprised in the second hole; and
  iii) at least one intermediate layer located between the first and the second layer, wherein the at least one intermediate layer comprises an intermediate ceramic, at least one intermediate hole and at least one intermediate cermet element comprised in the at least one intermediate hole;
wherein a projection of a cross-section of the first hole and a projection of a cross section of the second hole onto a plane $P_{x,y}$ are arranged offset to each other;
wherein the ceramic body comprises the ceramic of the individual layers; and
wherein the at least one cermet conductor is an electrical connection between the first cermet element and the second cermet element via the at least one intermediate cermet element and wherein the electrical connection is accomplished by an at least partial overlap of cermet elements in layers that are located adjacent to each other.

2. The composite according to claim 1, wherein the layer sequence of the composite comprises at least 2 intermediate layers that are arranged on top of each other forming an interlayer stack that is located between the first and the second layer, wherein the electrical connection within the layer stack is accomplished by an at least partial overlap of the intermediate cermet elements in intermediate layers that are located adjacent to each other.

3. The composite according to claim 1, wherein the center of a projection of the cross section of the first hole onto a plane $P_{x,y}$ is located at position $x_1,y_1$, the center of a projection of the cross section of the second hole onto the plane $P_{x,y}$ is located at position $x_2,y_2$, and wherein $x_1 \neq x_2$ and $y_1 = y_2$,
$x_1 \neq x_2$ and $y_1 \neq y_2$, or
$x_1 = x_2$ and $y_1 \neq y_2$.

4. The composite according to claim 1, wherein a cross section of the projection of at least one intermediate hole onto the plane $P_{x,y}$ has a length L and a width W, with $L \geq 2 \times W$.

5. The composite according to claim 4, wherein at least one intermediate hole comprises, at least at one end of the at least one intermediate hole, a portion that in a projection onto plane $P_{x,y}$ has a geometrical shape with a width $W_{portion}$, wherein $W_{portion} > W$ and wherein the at least partial overlap of intermediate cermet element in the intermediate layers that are located adjacent to each other is formed in the area of this portion.

6. The composite according to claim 5, wherein the portion has in a projection onto plane $P_{x,y}$ the form of a circle having a diameter $W_{portion}$.

7. The composite according to claim 6, wherein the at least one intermediate hole has in a projection onto plane $P_{x,y}$ the form of a dumbbell.

8. The composite according to claim 1, wherein at least one intermediate cermet element is an elongated body having a length L in the range from 20 to 10000 µm and a width W in the range from 10 to 1000 µm.

9. The composite according to claim 1, wherein the ceramic body and the conductor are each in one piece.

10. The composite according to claim 1, wherein the composite is coupled between an electrode and an implantable electrical medical device to electrically connect them.

11. A method for producing a composite, comprising:
I) providing a first ceramic green sheet, comprising a first hole and a first ceramic green sheet surface, filling the first hole with a first cermet precursor composition and drying the first cermet precursor composition;
II) providing at least one intermediate ceramic green sheet, comprising at least one intermediate hole, filling the at least one intermediate hole with an intermediate cermet precursor composition and drying the intermediate cermet precursor composition;
III) providing a second ceramic green sheet, comprising a second hole and a second ceramic green sheet surface, filling the second hole with a second cermet precursor composition and drying the second cermet precursor composition;
IV) arranging the first ceramic green sheet, the at least one intermediate ceramic green sheet and the second ceramic green sheet in a sequence such that the at least one intermediate ceramic green sheet is located between the first and the second ceramic green sheet;
V) firing the sequence of ceramic green sheets thereby obtaining a composite comprising a ceramic body and a cermet conductor
wherein the holes in the individual green sheets are located and formed in such a way that:
a projection of the cross section of the first hole and a projection of the cross-section of the second hole onto a plane $P_{x,y}$ are arranged offset to each other; and
in the ceramic body the cermet conductor is formed by an electrical connection between the first cermet element that in V) is formed in the first hole and the second cermet element that in V) is formed in the second hole via the at least one intermediate cermet element that in V) is formed in the at least one intermediate hole and wherein the electrical connection is accomplished by an at least partial overlap of the cermet elements in the layers that are located adjacent to each other.

12. The method according to claim 11, wherein in II) at least 2 intermediate ceramic green sheets are provided, wherein in IV) the at least 2 intermediate ceramic green sheets are arranged on top of each other forming an intermediate ceramic green sheet stack that is located between the first and the second ceramic green sheet, wherein the electrical connection within the intermediate layer stack that in V) is derived from the intermediate ceramic green sheet stack is accomplished by an at least partial overlap of the intermediate cermet elements in intermediate layers that are located adjacent to each other.

13. The method according to claim 11, wherein in the composite the center of a projection of the cross section of the first hole onto a plane $P_{x,y}$ is located at position $x_1,y_1$ and the center of a projection of the cross section of second hole onto plane $P_{x,y}$ is located at position $x_2,y_2$, wherein $x_1 \neq x_2$ and $y_1 = y_2$,
$x_1 \neq x_2$ and $y_1 \neq y_2$ or
$x_1 = x_2$ and $y_1 \neq y_2$.

14. The method according to claim 11, wherein a cross section of the projection of at least one intermediate hole onto the plane $P_{x,y}$ has a length L and a width W, with $L \geq 2 \times W$, and wherein at least one intermediate cermet element is an elongated body having a length L in the range from 20 to 10000 µm and a width W in the range from 10 to 1000 µm.

15. A composite obtainable by the method according to claim 11.

16. A device comprising a housing, an inner volume, an outer volume, and the composite according to claim 1;
wherein the housing
α1) encloses the inner volume,
α2) separates the inner volume from the outer volume, and
α3) comprises an aperture,
wherein the aperture frames the composite.

* * * * *